(12) United States Patent
Kaufmann et al.

(10) Patent No.: US 12,616,506 B2
(45) Date of Patent: May 5, 2026

(54) MATERIAL DIRECTING ORTHOPEDIC ANCHOR

(71) Applicant: GENESYS SPINE, Austin, TX (US)

(72) Inventors: Josh Kaufmann, Austin, TX (US); Landon Gilkey, Austin, TX (US); Francois Follini, Austin, TX (US); Greg Calbert, Austin, TX (US); Scott Bryant, Austin, TX (US); Brian Bergeron, Austin, TX (US); Kaywan Gamadia, Cape Girardeau, MO (US); Maahir Haque, Orlando, FL (US)

(73) Assignee: GENESYS SPINE, Austin, TX (US)

( * ) Notice: Subject to any disclaimer, the term of this patent is extended or adjusted under 35 U.S.C. 154(b) by 168 days.

(21) Appl. No.: 18/420,886

(22) Filed: Jan. 24, 2024

(65) Prior Publication Data

US 2024/0206919 A1     Jun. 27, 2024

Related U.S. Application Data

(63) Continuation of application No. 16/967,007, filed as application No. PCT/US2019/016183 on Jan. 31, 2019, now Pat. No. 11,883,077.

(Continued)

(51) Int. Cl.
    *A61B 17/70*        (2006.01)
    *A61B 17/86*        (2006.01)
(52) U.S. Cl.
    CPC ........ *A61B 17/7055* (2013.01); *A61B 17/863* (2013.01); *A61B 17/864* (2013.01)
(58) Field of Classification Search
    None
    See application file for complete search history.

(56) References Cited

U.S. PATENT DOCUMENTS 5,129,904 A * 7/1992 Illi ...................... A61B 17/864
                                              606/907
5,695,497 A * 12/1997 Stahelin .............. F16B 23/0007
                                              606/104

(Continued)

FOREIGN PATENT DOCUMENTS

EP        2645946        1/2017
WO      2014149746 A1    9/2014

OTHER PUBLICATIONS

International Searching Authority, "Notification of Transmittal of the International Search Report and the Written Opinion of the International Searching Authority," mailed May 20, 2019, in International application No. PCT/US2019/016183.

(Continued)

*Primary Examiner* — Zade Coley
(74) *Attorney, Agent, or Firm* — Trop, Pruner & Hu, P.C.

(57)                    ABSTRACT

An embodiment includes a sacroiliac joint bone anchor system comprising: a bone anchor including an outer surface and an inner surface; wherein (a)(i) the outer surface includes a proximal third, a middle third, and a distal third, (a)(ii) the middle third of the outer surface includes at least one aperture that couples the outer surface to the inner surface; (a)(iii) the proximal third of the outer surface includes proximal threads, and (a)(iv) the distal third of the outer surface includes distal threads; wherein (b)(i) the bone anchor is cannulated, (b)(ii) a channel is located on the inner surface, (b)(iii) the channel extends from a proximal third of the inner surface to a distal third of the inner surface, and (b)(iv) the channel provides at least one half a rotation about a long axis of the bone anchor.

19 Claims, 8 Drawing Sheets

Related U.S. Application Data

(60) Provisional application No. 62/625,157, filed on Feb. 1, 2018.

(56) References Cited

U.S. PATENT DOCUMENTS

| | | | |
|---|---|---|---|
| 6,981,974 B2 * | 1/2006 | Berger .................. A61B 17/82 |
| | | | 411/397 |
| 8,840,651 B2 | 9/2014 | Reiley | |
| 9,358,057 B1 | 6/2016 | Whipple et al. | |
| 9,526,547 B2 | 12/2016 | Reed | |
| D783,821 S | 4/2017 | Folsom et al. | |
| 9,675,394 B2 | 6/2017 | Reiley | |
| 9,820,789 B2 | 11/2017 | Reiley | |
| 9,839,448 B2 | 12/2017 | Reckling et al. | |
| 9,943,340 B2 | 4/2018 | Whipple et al. | |
| D816,843 S | 5/2018 | Lewis | |
| 10,064,670 B2 | 9/2018 | Mootien et al. | |
| 10,179,014 B1 * | 1/2019 | Menmuir ............ A61B 17/864 | |
| 10,595,917 B2 | 3/2020 | Loftus | |
| 11,129,655 B2 | 9/2021 | Crossgrove et al. | |
| 11,147,688 B2 | 10/2021 | Reckling et al. | |
| 11,234,830 B2 | 2/2022 | Mesiwala et al. | |
| 2004/0147929 A1 * | 7/2004 | Biedermann ........ A61B 17/864 |
| | | | 623/17.11 |
| 2006/0106390 A1 * | 5/2006 | Jensen ............... A61B 17/8685 |
| | | | 606/328 |
| 2012/0197311 A1 * | 8/2012 | Kirschman ........ A61B 17/7098 |
| | | | 606/104 |
| 2014/0066758 A1 * | 3/2014 | Marik ................ A61B 17/7064 |
| | | | 600/431 |
| 2015/0327903 A1 | 11/2015 | Brown et al. | |
| 2016/0287301 A1 * | 10/2016 | Mehl ................. A61B 17/8685 |

OTHER PUBLICATIONS

Spine Med, "Treatments—Sacroiliac Joint Fusion," Jan. 12, 2018, 4 pages.

* cited by examiner

MATERIAL DIRECTING ORTHOPEDIC ANCHOR

PRIORITY

This application is a continuation of U.S. patent application Ser. No. 16/967,007, filed Aug. 3, 2020, which is a § 371 national stage of international application PCT/US2019/016183, filed Jan. 31, 2019, which claims priority to U.S. Provisional Patent Application No. 62/625,157 filed on Feb. 1, 2018 and entitled "Material Directing Orthopedic Anchor". The content of each of the above applications is hereby incorporated by reference.

TECHNICAL FIELD

Embodiments of the invention are in the field of orthopedic implants.

BACKGROUND

The sacroiliac joint (SI joint) is a joint in the pelvis that connects the sacrum and the ilium. When ligaments of the joint become loose or otherwise dysfunctional the SI joint may fail to provide adequate shock absorption for the spine, which may be painful. SI joint fusion is a technique used to stabilize the SI joint and to alleviate pain caused by the dysfunctional joint. One surgical technique for fusion is to drive one or more compression screws across the joint to stabilize the joint. Afterwards bone graft is placed within the joint, which eventually leads to fusion of the joint and, ideally, less pain.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical contact with each other and "coupled" may indicate elements co-operate or interact with each other, but they may or may not be in direct physical contact. Phrases such as "comprising at least one of A and B" include situations with A, B, or A and B.

An embodiment provides an anchor. One example of an anchor is a screw. Other examples include nails and the like. An embodiment includes a screw with an inner geometry that directs bone particulate in a general direction. For example, the inner geometry may include flutes formed from cuts and/or channels.

Figure 1A:
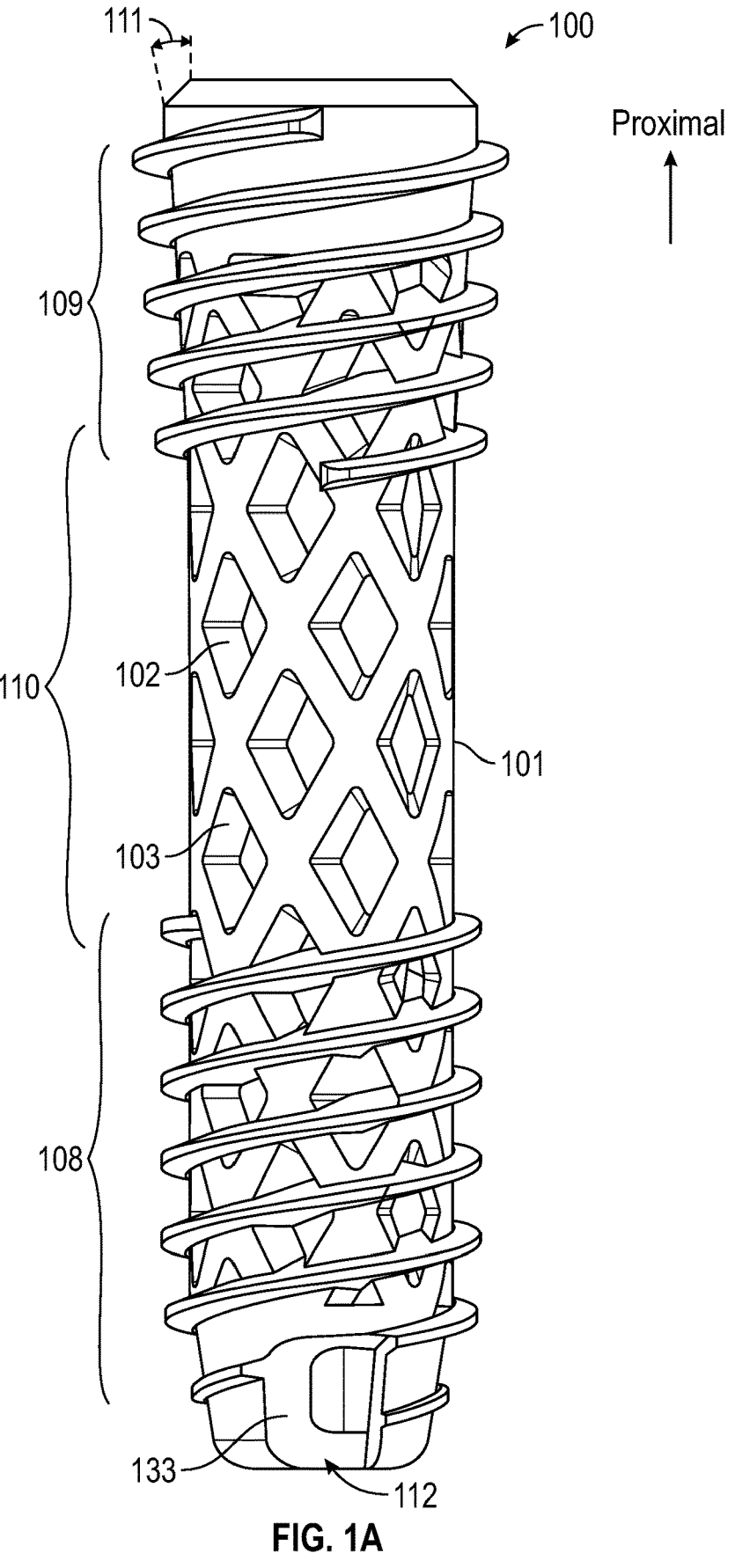
FIGS. 1A, 1B, 1C provide differing views of an embodiment.
Figure 1B:
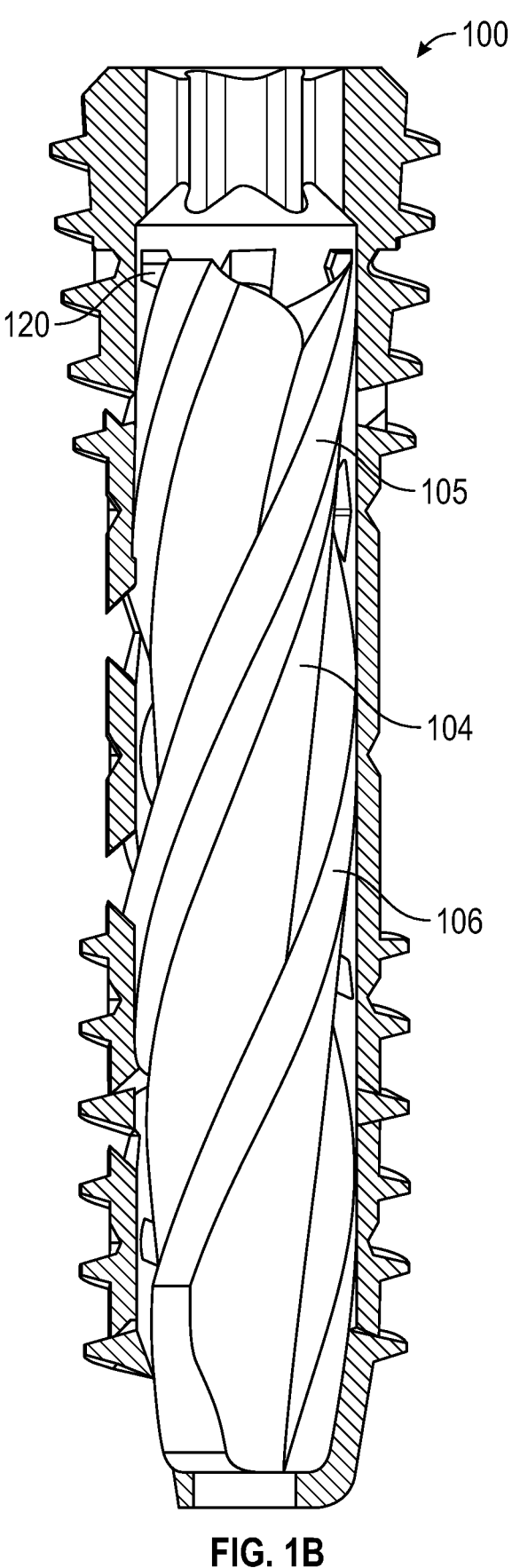
Figure 1C:
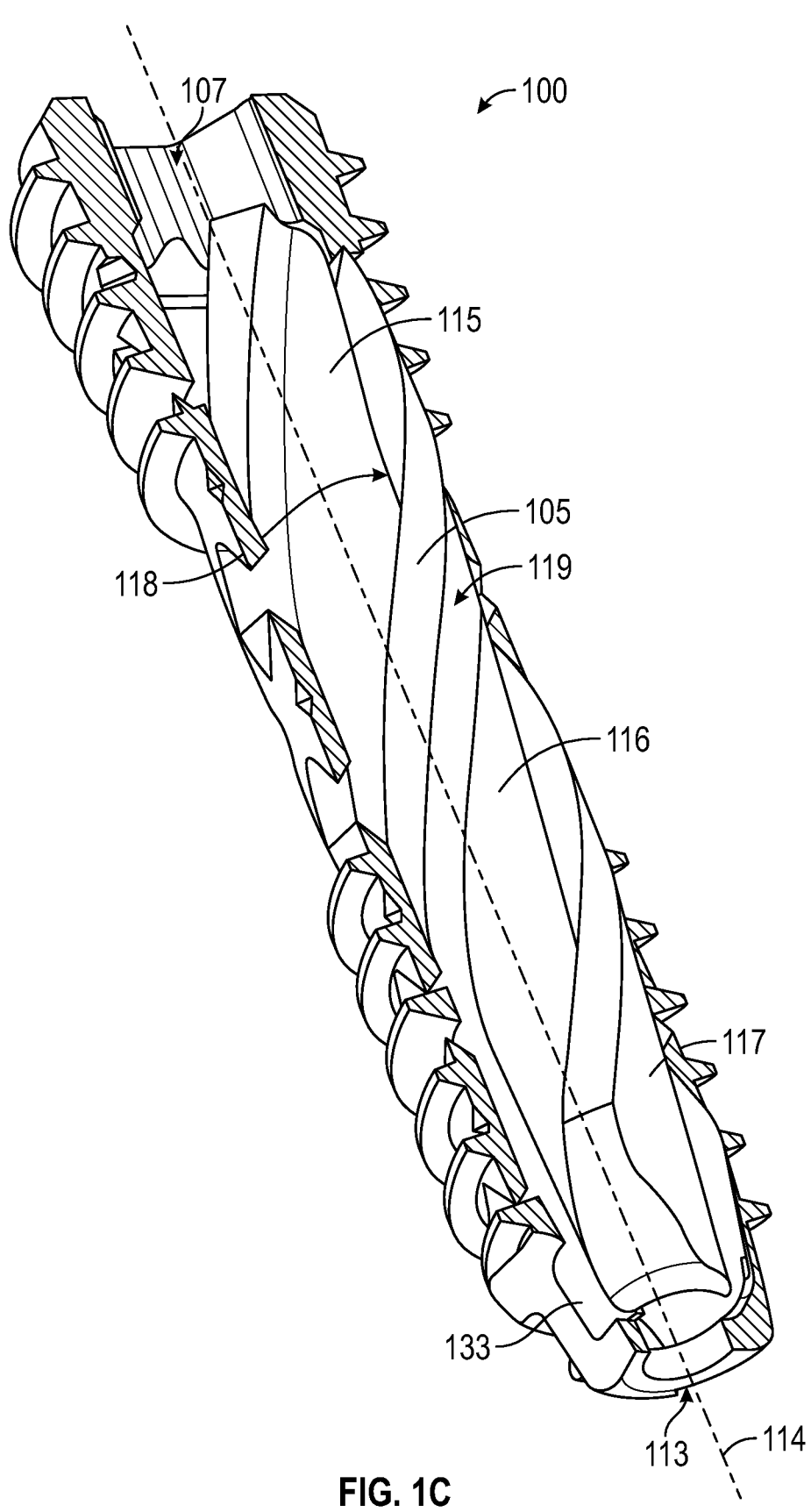

For example, FIGS. 1A, 1B, and 1C show varying views of an embodiment. FIG. 1A includes a side view, FIG. 1B includes a side view with the exterior shell (or conduit or housing) removed to better visualize the inner bone particulate conveyor flutes, and FIG. 1C includes a perspective view with the exterior shell removed to better visualize the inner bone particulate conveyor flutes An outer shell 101 (which may also be referred to as a conduit) may have various apertures or windows, two of which are shown at apertures 102, 103. These apertures allow bone fusion to occur between the pelvic bone and bone particulate located within a trough or channel of a flute, such as channel 104 (which is located between flute ridges 105, 106). Screw 100 includes a receptor 107 that mates with a driver head. In an embodiment screw 100 includes proximal threads 109 and distal threads 108. The threads 108, 109 may be separated from one another by a threadless region 110, but in other embodiments threads may run from the distal end region to the proximal end region. Screw 100 may include areas of taper based in part on, for example, the angle of taper 111. The tapered wall may extend only along the region with proximal threads 109 or may extend within regions 108, 109, and/or 110 in other embodiments. Screw 100 may include an aperture 112 that provides an entry from outside screw 100 to inside screw 100, such that once bone particulate enters aperture 112 it may move along various lengths of channel 104. Afterwards the bone particulate will allow for fusion via apertures 102 and/or 103.

Some embodiments may provide apertures within the inner wall that defines channel 104. For example, screw 100 is cannulated with an aperture 113 that couples the proximal and distal ends of the screw along long axis 114. In an embodiment, apertures may couple channel 104 to the hollow channel 113 at locations such as, for example, locations 115, 116, and/or 117. Channel 113 may cooperate with a guide wire.

An embodiment may include apertures within a ridge. For example, apertures may be located at locations 118, 119 of ridge 105. The apertures 118, 119 may completely traverse ridge 105.

Thus, an embodiment directs materials to a location. That material may be bone particulate created by rotation of the screw itself. The location may be various points within channel 104 that are proximal to aperture 112.

Embodiments may direct material inward, upward (e.g., from a distal portion of channel 104 to a proximal portion of channel 104), or outward. For example, by altering the geometry of ridges 105, 106 (e.g., turning the ridges to project material inward) material may be directed inward (i.e., into channel 113) via apertures located at positions 115, 116. By altering the geometry of ridges 105, 106 (e.g., turning the ridges to project material outward) material may be directed outward via apertures that couple channel 104 to an exterior at, for example, locations near a proximal end of screw 100. Such locations may be included in region 120.

Embodiments described herein address problems recognized by Applicant. For example, Applicant determined that when using a conventional screw (or tap) material is directed outward or only onto the outer annulus of the tool. This may promote bone growth about the exterior of the implant but not necessarily within the implant. Further, Applicant determined that by providing an outer structure that is porous (e.g., has apertures coupling the inside of the middle of the screw to the outside of the middle of the screw) bone can grow through the implant. However, Applicant further realized that if, for example, the middle regions of the screw lack bone particulate (because particulate is blocked from getting to this exemplar middle region), this absence of particulate may restrict or stop the full formation of bone ingrowth near those apertures in the middle of the screw.

In contrast, in an embodiment the outer annulus remains intact to "advance" the overall body of the screw (e.g., thread portions 108, 109), but the inner geometry can direct particulate into a predetermined location via channel 104 and ridges 105, 106. The inner flute directs drilled bone particulate to the middle portion of the screw so any apertures in the middle of the screw (e.g., apertures 102, 103 which couple the outside of the screw to the inside of the screw) can locate bone particulate near exterior bone, thereby allowing for faster bone ingrowth into the screw.

While the above example concerns apertures (wherein the apertures couple the outside of the screw to the inside of the screw) in the middle of the screw, this is just an example and the same principle may be applied to apertures in the proximal or distal regions of the screw or anchor.

Embodiments provide various advantages. For example, embodiments distribute bone particulate along the length of the anchor. Further, that particulate is exterior to window 102 and interior to window 102 (which promotes bone in-growth to the anchor). Further, this distribution of bone particulate occurs "automatically" or in response to simply drilling the anchor into bone and generating bone particulate. Also, while SI fusion is a challenging procedure involving placing implants across a joint, by providing both (a) fixation with the screw shape (e.g., via threads and tapering), and (b) bone graft channeling (e.g., via channel 104), the fusion rate and ease of use for the surgeon will accelerate.

Figure 2B:
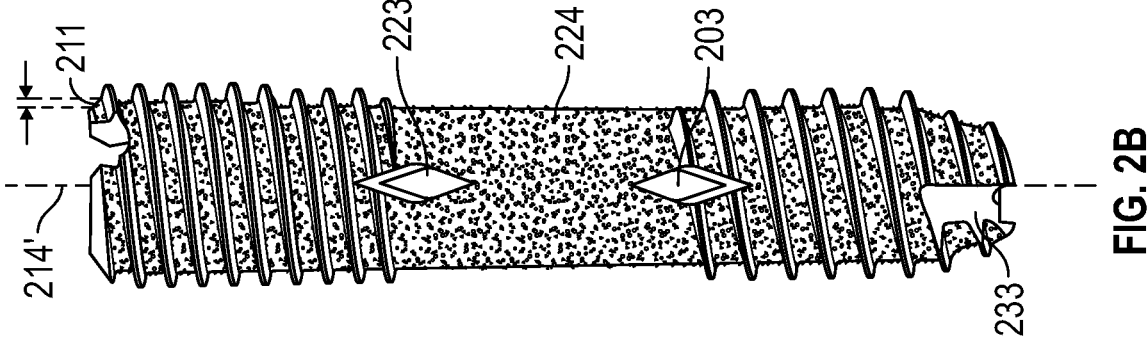
FIGS. 2A, 2B, 2C provide differing views of an embodiment.
Figure 2A:
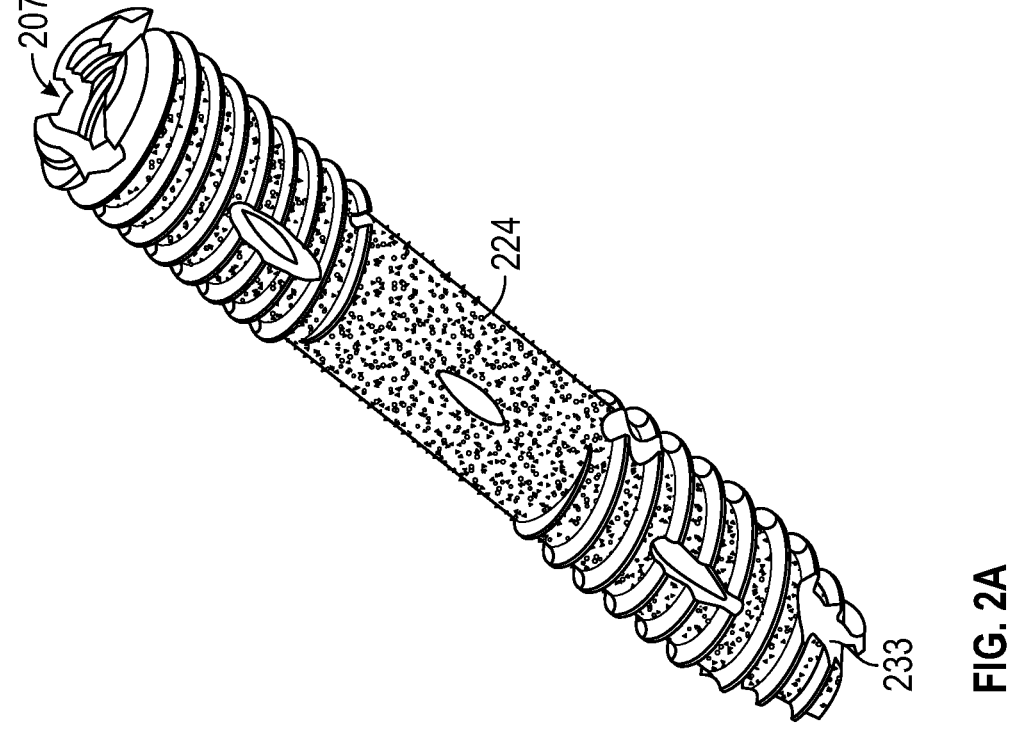
Figure 2C:
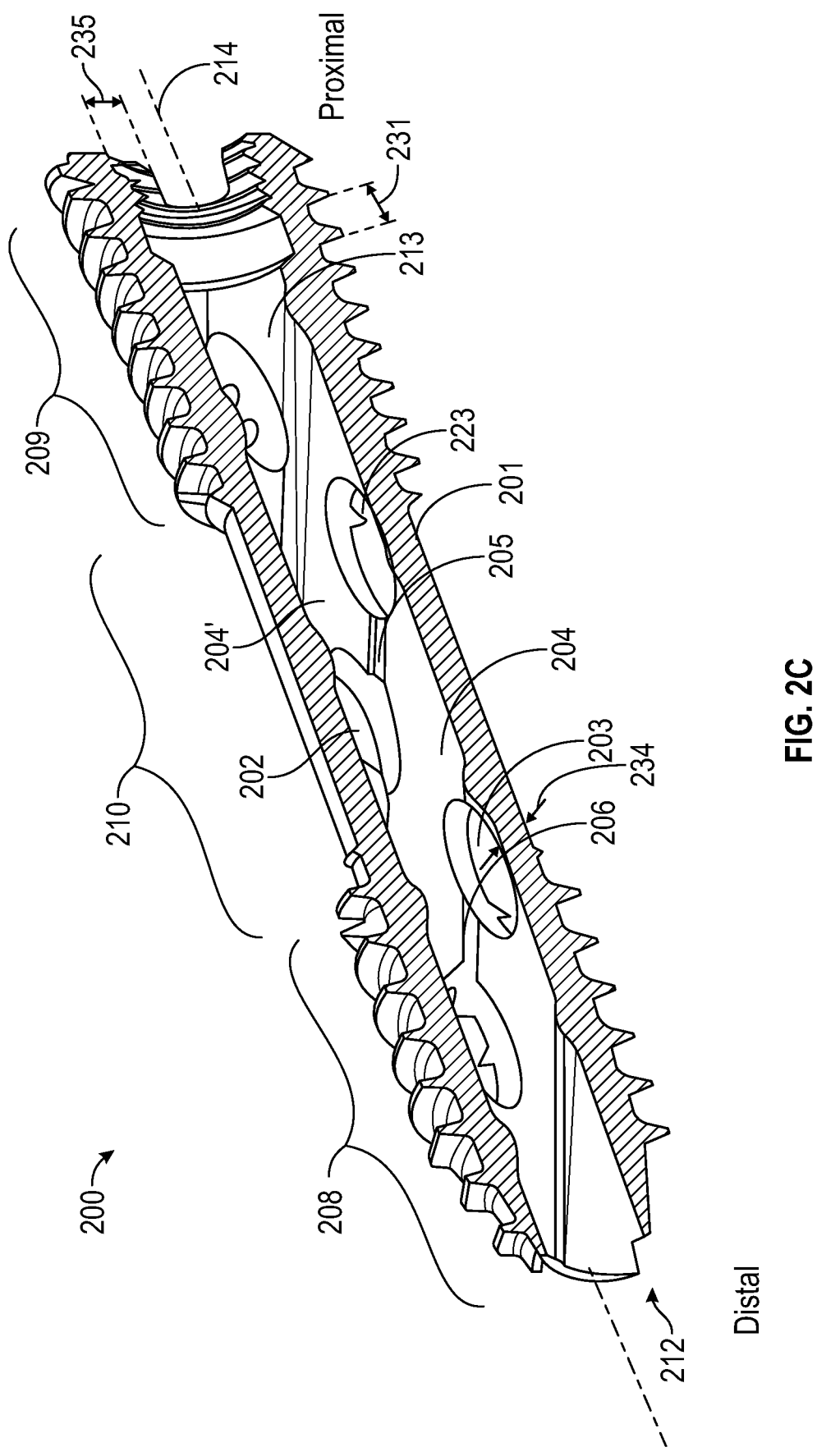

For example, FIGS. 2A, 2B, and 2C show varying views of an embodiment. FIG. 2A includes a perspective view, FIG. 2B includes a side view, and FIG. 2C includes a perspective cross-sectional view.

An outer shell 201 (which may also be referred to as a conduit) may have various apertures or windows, two of which are shown at apertures 202, 203. These apertures allow bone fusion to occur between the pelvic bone and bone particulate located within a trough or channel of a flute, such as channel 204 (which is located between flute ridges 205, 206). Screw 200 includes a receptor 207 that mates with a driver head. In an embodiment screw 200 includes proximal threads 209 and distal threads 208. The threads 208, 209 may be separated from one another by a threadless region 210, but in other embodiments threads may run from the distal end region to the proximal end region. Screw 200 may include areas of taper based in part on, for example, the angle of taper 211. The tapered wall may extend only along the region with proximal threads 209 or may extend within regions 208, 209, and/or 210 in other embodiments. Screw 200 may include an aperture 212 that provides an entry from outside screw 200 to inside screw 200, such that once bone particulate enters aperture 212 it may move along various lengths of channel 204. Afterwards the bone particulate will allow for fusion via apertures 202 and/or 203.

Screw 200 is cannulated with an aperture 213 that couples the proximal and distal ends of the screw along long axis 214. In an embodiment, channel 204 defines the outer boundaries of hollow channel 213. Channel 213 may cooperate with a guide wire, Kirschner wire (K-wire).

In an embodiment apertures may be formed within a ridge. For example, aperture 202 interfaces ridge 205 as well as channel 204. The apertures 202, 203 may respectively and completely traverse ridges 205, 206.

Thus, an embodiment directs materials to a location. That material may be bone particulate created by rotation of the screw itself. The location may be various points within channel 204 that are proximal to aperture 212.

Embodiments described herein address problems recognized by Applicant. For example, Applicant determined that when using a conventional screw (or tap) material is directed outward or only onto the outer annulus of the tool. This may promote bone growth about the exterior of the implant but not necessarily within the implant. Further, Applicant determined that by providing an outer structure that is porous (e.g., has apertures coupling the inside of the middle of the screw to the outside of the middle of the screw) bone can grow through the implant. However, Applicant further realized that if, for example, the middle regions of the screw lack bone particulate (because particulate is blocked from getting to this exemplar middle region), this absence of particulate may restrict or stop the full formation of bone ingrowth near those apertures in the middle of the screw.

In contrast, in an embodiment the outer annulus remains intact to "advance" the overall body of the screw (e.g., thread portions 108, 109), but the inner geometry can direct particulate into a predetermined location via channel 104 and ridges 105, 106. The inner flute directs drilled bone particulate to the middle portion of the screw so any apertures in the middle of the screw (e.g., apertures 102, 103 which couple the outside of the screw to the inside of the screw) can locate bone particulate near exterior bone, thereby allowing for faster bone ingrowth into the screw.

While the above example concerns apertures (wherein the apertures couple the outside of the screw to the inside of the screw) in the middle of the screw, this is just an example and the same principle may be applied to apertures in the proximal or distal regions of the screw or anchor.

Embodiments provide various advantages. For example, embodiments distribute bone particulate along the length of the anchor. Further, that particulate is exterior to window 102 and interior to window 102 (which promotes bone in-growth to the anchor). Further, this distribution of bone particulate occurs "automatically" or in response to simply drilling the anchor into bone and generating bone particulate. Also, while SI fusion is a challenging procedure involving placing implants across a joint, by providing both (a) fixation with the screw shape (e.g., via threads and tapering), and (b) bone graft channeling (e.g., via channel 104), the fusion rate and ease of use for the surgeon will accelerate.

Apertures 203, 223 may be formed along a linear trajectory. The outer surface 224 of the screw 200 may be roughened with bumps to promote bone fusion.

Figure 4:
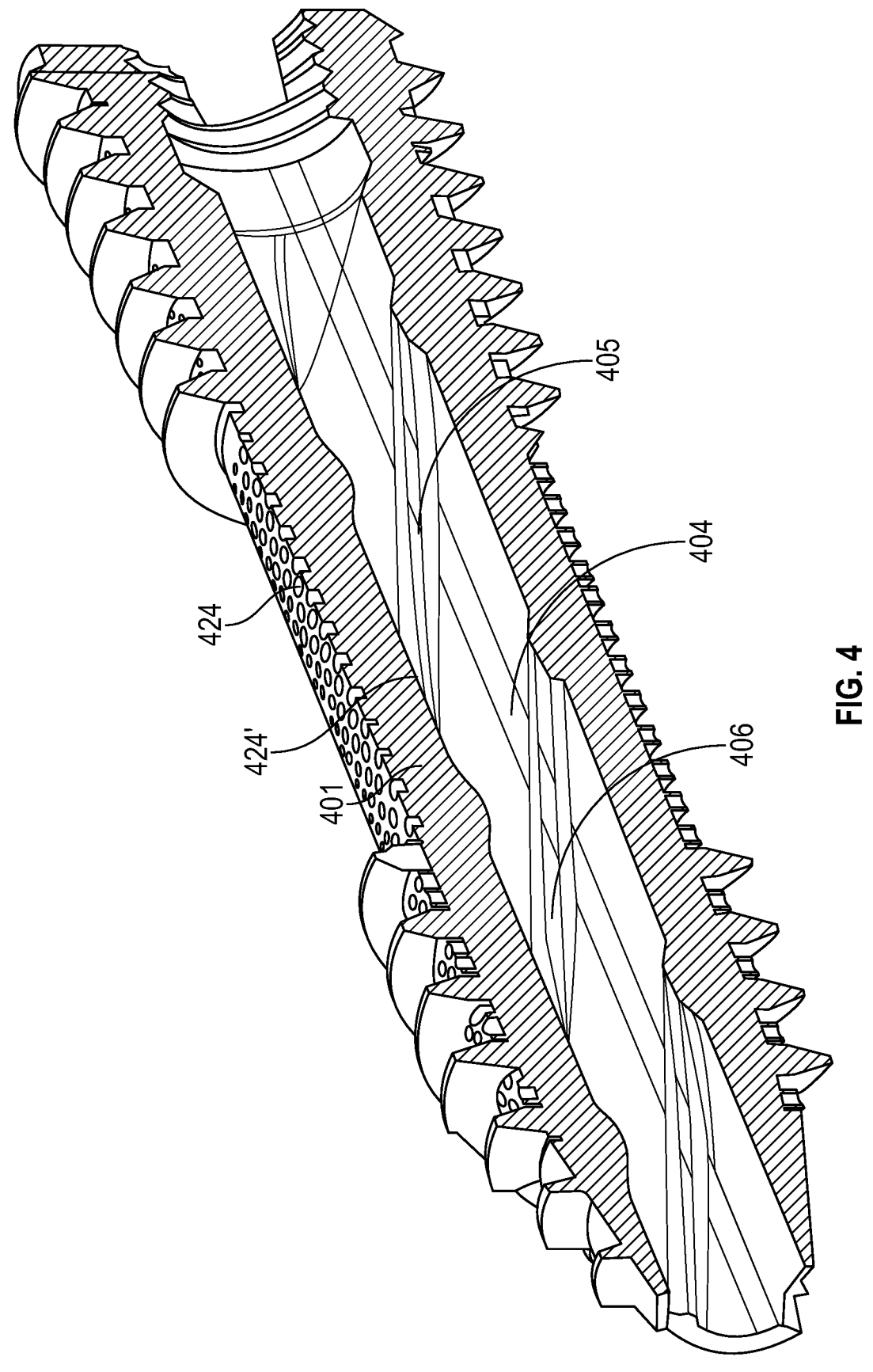
FIG. 4 includes a cross-sectional view of an embodiment.

FIG. 4 depicts an embodiment with an outer surface 424 with a series of apertures that do not traverse shell 401. Outer surface 424 is opposite inner surface 424'. Inner surface 424' includes channel 404 between ridges 405, 406.

Figures 3A, 3B, 3C, 3D:
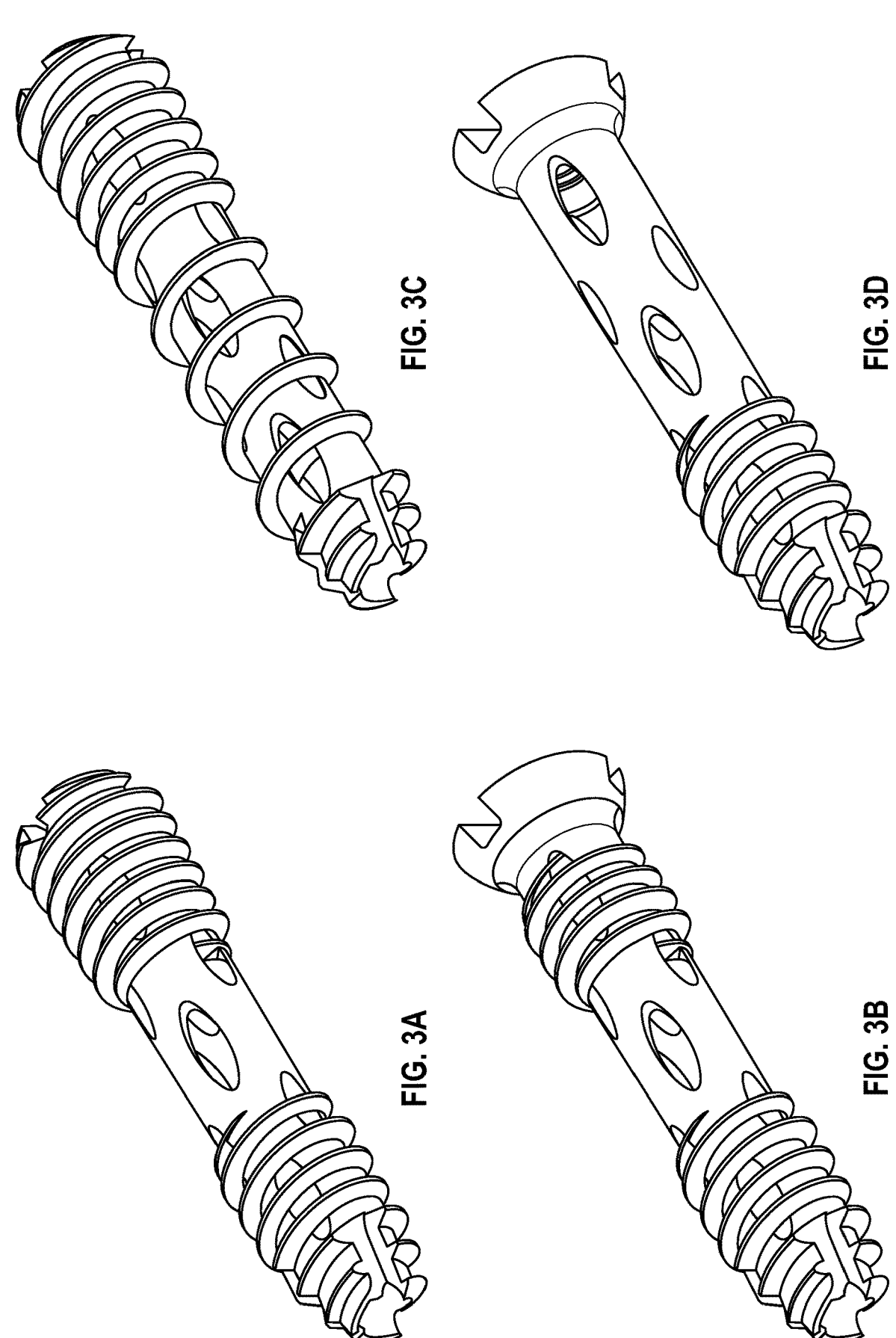
FIGS. 3A, 3B, 3C, 3D provide embodiments with varying thread configurations and/or tool fixation configurations.

FIG. 3A includes an outer surface that is smooth. FIG. 3B includes a tool receptor with a wider profile than that of receptor 107. FIG. 3C includes an embodiment with threads that extend along the entire length of the screw. The threads have areas of different pitch (different crest to crest distance). FIG. 3D includes an embodiment with threads restricted to a distal half of the screw.

Embodiments may be formed via additive manufacturing (e.g., 3-D printing) using materials such as titanium, stainless steel, or various medical grade materials including combinations thereof (e.g., alloys).

While various embodiments described herein address fixating a SI joint, other embodiments are not so limited and may be used generally to couple tissues together, such as two portions of bone or other tissue. Those portions need not be on opposite sides of a joint. For example, an anchor embodiment described herein could be used as a shank of a pedicle screw. Other embodiments may be used for surgery of the shoulder, wrist, toe (i.e., anywhere an implant is placed where bone is directed from one location to the internal flute of the implant to facilitate fusion).

As used herein, a compression screw compresses two articles against one another when the screw is drilled across a seam that exists between the two articles.

As used herein, a flute includes a groove in a column (e.g., conduit).

An embodiment includes a method. The physician inserts a pin into the patient's bone and then locates a dilator over the pin (which may also be referred to as a wire). Other dilators may then be located over the pin. The physician then locates a drill guide over one of the dilators. A drill is then used in conjunction with the drill guide. The drill may then be removed and a bone anchor may be advanced over the pin using an anchor inserter. The inserter may have threads that couple to internal threads, such as those shown in the proximal portion of FIG. 2A. The anchor is advanced into the ilium, across the SI joint, and into the sacrum.

The following examples pertain to further embodiments.

Example 1. A bone anchor system comprising: a bone anchor including an outer surface and an inner surface; wherein (a)(i) the outer surface includes a proximal third, a middle third, and a distal third, (a)(ii) the middle third of the outer surface includes at least one aperture that couples the outer surface to the inner surface; (a)(iii) the proximal third of the outer surface includes proximal threads, and (a)(iv) the distal third of the outer surface includes distal threads; wherein (b)(i) the bone anchor is cannulated, (b)(ii) a channel is located on the inner surface, (b)(iii) the channel extends from a proximal third of the inner surface to a distal third of the inner surface, and (b)(iii) the channel provides at least one half a rotation about a long axis of the bone anchor.

For example, see FIG. 2C where aperture 202 couples outer surface to the inner surface. Channel 204 is located on the inner surface and is between ridges 205, 206.

In the embodiment of FIG. 2C channel 204 is monolithic with the threads and outer surface of the anchor. In the embodiment of FIG. 2C the entire anchor is monolithic and formed via additive manufacturing. However, in another embodiment portions may be not necessarily be monolithic with each other. For instance, an embodiment may include an internal auger (with a channel similar to channel 104 or 204) to advance bone particulate. That auger may be nonmonolithic with the outer surface and threads. The inner auger may rotate independently from the outer surface of the anchor. For example, the internal auger could be driven at a different speed from external surface. In an embodiment, the anchor of FIG. 1C is monolithic. However, in another embodiment portion 101 (outer shell) rotates independently of an inner auger that may include channel 104.

Another version of Example 1. A bone anchor system comprising: a bone anchor including an outer surface and an inner surface; wherein (a)(i) the outer surface includes a proximal third, a middle third, and a distal third, (a)(ii) the middle third of the outer surface includes at least one aperture that couples the outer surface to the inner surface; (a)(iii) the proximal third of the outer surface includes proximal threads, and (a)(iv) the distal third of the outer surface includes distal threads; wherein (b)(i) the bone anchor is cannulated, (b)(ii) a channel is located on the inner surface, and (b)(iii) the channel extends from a proximal third of the inner surface to a distal third of the inner surface.

Another version of Example 1. A bone anchor system comprising: a bone anchor including an outer surface and an inner surface; wherein (a)(i) the outer surface includes a proximal third, a middle third, and a distal third, (a)(ii) the middle third of the outer surface includes at least one aperture that couples the outer surface to the inner surface; (a)(iii) the proximal third of the outer surface includes proximal threads, and (a)(iv) the distal third of the outer surface includes distal threads; wherein (b)(i) the bone anchor is cannulated, (b)(ii) means for conveying bone particulate proximally within the bone anchor, (b)(iii) the channel extends from a proximal third of the inner surface to a distal third of the inner surface, (b)(iv) the means for conveying bone particulate proximally within the bone anchor is located on the inner surface.

In this alternative version of Example 1, the channel does not necessarily "rifle" or rotate along the inner surface. For example, the channel may have straight ridges that are parallel to the long axis.

Ridges of the channel are not necessarily continuous and may include interruptions or breaks. Ridges may be formed by bumps of varying length.

Not all embodiments include apertures such as apertures 202, 203.

Example 2. The bone anchor system of claim 1 wherein a plane, orthogonal to the long axis of the bone anchor, intersects each of: (c)(i) the outer surface, (c)(ii) at least one of the at least one aperture that couples the outer surface to the inner surface; and (c)(iii) the channel.

Example 3. The bone anchor system of claim 2 comprising a distal aperture in a distal third of the bone anchor, wherein the distal aperture is configured to advance bone particulate from outside the bone anchor to the channel.

For example, see aperture 212.

Another version of Example 3. The bone anchor system of claim 2 comprising a distal aperture in a distal third of the bone anchor, wherein the distal aperture includes a means for advancing bone particulate from outside the bone anchor to the channel.

Example 4. The bone anchor system of claim 2, wherein the bone anchor is a compression screw.

Another version of Example 4. The bone anchor system of claim 2, wherein the bone anchor is a sacroiliac joint screw.

Example 5. The bone anchor system of claim 2, wherein: the at least one aperture includes a first aperture and a second aperture; the first aperture includes a long axis parallel to the long axis of the bone anchor; the first aperture includes a short axis orthogonal to the long axis of the first aperture; the first aperture includes a length measured along the long axis and a width measured along the short axis; the length of the first aperture is greater than the width of the first aperture.

For example, see apertures 202, 203. Aperture 202 is somewhat ovular and has a length greater than its width. Such an aperture design balances an increase in area for bone fusion while maintaining strength in the anchor.

Example 6. The bone anchor system of claim 5 wherein: an additional axis is parallel to the long axis of the bone anchor; the additional axis intersects the first and second apertures.

For example, see axis 214' of FIG. 2B.

Example 7. The bone anchor system of claim 5 comprising an additional channel located on the inner surface, wherein: (b)(i) the additional channel extends from the proximal third of the inner surface to the distal third of the inner surface, and (b)(ii) the additional channel provides at least one half a rotation about the long axis of the bone anchor.

For example, see channel 204'.

Example 8. The bone anchor system of claim 7 comprising a ridge on the inner surface, wherein: the ridge forms a wall of the channel; the ridge forms an additional wall of the additional channel.

For example, see ridge 205.

Example 9. The bone anchor system of claim 8, wherein: the bone anchor includes a proximal tip and a distal tip; the distal third of the outer surface includes a distal aperture in addition to the at least one aperture; the distal aperture is between the proximal and distal tips of the bone anchor; the distal aperture directly connects to the channel; an opening of the distal aperture extends at least 1 mm proximally away from the distal tip and towards the proximal tip; the distal aperture is at least partially included in a sidewall of the bone anchor.

For example, see distal aperture 233 (or analogous aperture 133 in FIG. 1C). The sidewall includes outer surface of the anchor.

In other embodiments the aperture may extend between 0 and 1 mm, 1 and 3 mm, 2 and 4 mm, and the like proximally away from the distal tip and towards the proximal tip.

Such an embodiment may provide for "self-filling" wherein the anchor moves particulate into channel 204 and proximally towards 207 without the physician having to pack the particulate within the anchor (or at least providing some aid to the physician regarding advancing particulate within the anchor).

Example 10. The bone anchor system of claim 9, wherein: the distal third of the outer surface includes an additional distal aperture in addition to the at least one aperture; the additional distal aperture is between the proximal and distal tips of the bone anchor; the additional distal aperture directly connects to the additional channel; the additional distal aperture is at least partially included in the sidewall of the bone anchor.

Thus, one such aperture may feed particulate to channel 204 while another aperture feeds particulate to channel 204'.

Example 11. The bone anchor system of claim 10 wherein: the proximal threads include a first thread pitch which comprises a distance between crests of two adjacent threads; the distal threads include a second thread pitch; the first thread pitch is less than the second thread pitch.

For example, see first thread pitch 231.

Example 12. The bone anchor system of claim 11 comprising a rod, wherein: the rod includes a long axis; the rod includes a short axis orthogonal to the long axis of the rod; the rod includes a length measured along the long axis of the rod and a width measured along the short axis of the rod; the width of the rod the bone anchor includes a central aperture defined by the inner surface of the bone anchor and the central aperture extends from the proximal tip of the bone anchor to the distal tip of the bone anchor; the central aperture includes a width measured along a short axis of the bone anchor, the short axis of the bone anchor being orthogonal to the long axis of the bone anchor; the width of the rod is less than the width of the central aperture; the width of the rod is at least 75% of the width of the central aperture.

Figure 2D:
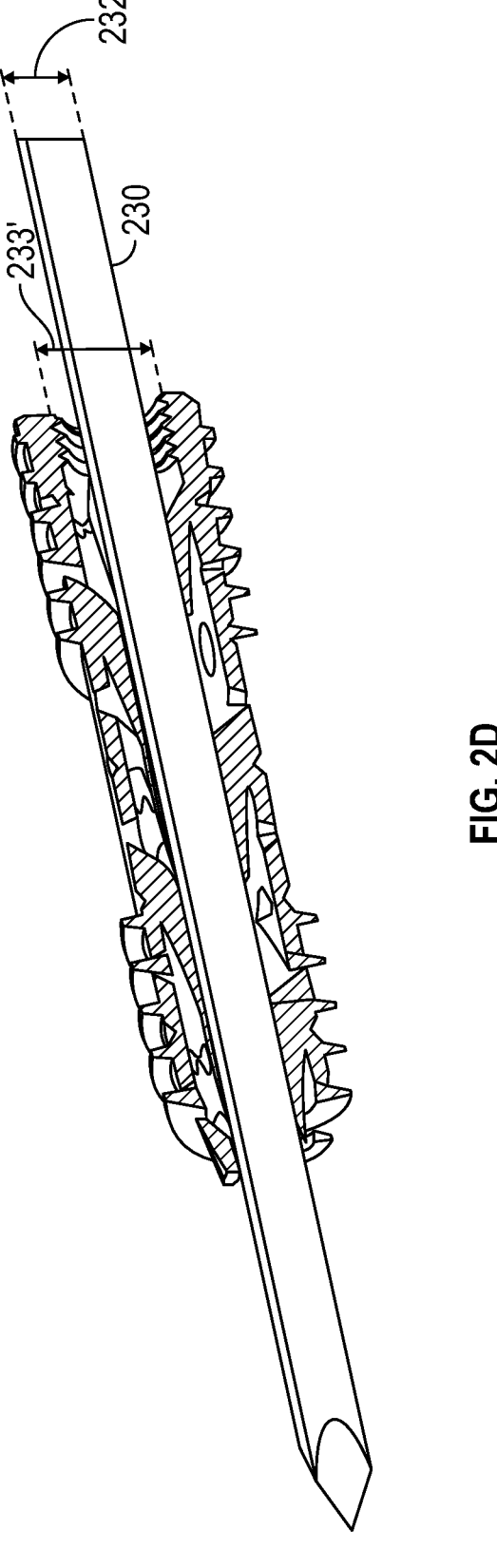
FIG. 2D provides a view of a rod or wire to be used with bone anchor embodiments described herein.

For example, see FIG. 2D with rod width 232 and central aperture width 233. In other embodiments the width of the rod is at least 50%, 60%, 70%, 80%, 90%, 98%, 99% of the width of the central aperture.

In an embodiment the rod includes channels instead of the bone anchor. In an embodiment the bone anchor and the rod both include channels. In some embodiments the channeling on the bone anchor is keyed to the channeling on the rod. When the rod is removed from the patient a tool holds the anchor in place so only the rod is removed and not the anchor.

In an embodiment, the rod width may be 0.125 inches (3.175 mm), the inner diameter of the channels (e.g., extending from an innermost part of a ridge to an opposing innermost part of a ridge) may be about 0.134 inches (3.4036 mm), and the inner diameter of the central aperture may be about 0.168 inches (4.2672 mm). Thus, with these dimensions there is a potential for binding but such potential is alleviated to some degree by the rifling or conveyance of bone particulate via the one or more channels. In an embodiment, the rod width may be between 3-5 mm, the inner diameter of the channels (e.g., extending from an innermost part of a ridge to an opposing innermost part of a ridge) may be about 3-6 mm, and the inner diameter of the central aperture may be about 4-7 mm.

An advantage of an embodiment such as anchor 200 is the ability to lessen binding. For example, the tolerance between rod 230 and anchor 200 is tight. This is to ensure the anchor is placed accurately with respect to the guiding rod or wire. As a consequence, bone particulate sometimes wedges between the inner wall of the anchor and the rod. With conventional anchor/rod systems this may lead to binding where the anchor is prevented or at least hindered from rotating about the rod during anchor implantation. However, due to channels such as channel 204 such binding is lessened or eliminated. For instance, if particulate is located between ridge 205 and the rod the particulate is quickly relocated to one of channels 204, 204' to lessen in binding.

Example 13. The bone anchor system of claim 11 wherein: the sidewall of the bone anchor includes a first thickness included in a proximal third of the bone anchor; the sidewall of the bone anchor includes a second thickness included in a distal third of the bone anchor; the first thickness and the second thickness are both measured orthogonal to the long axis of the bone anchor; the first thickness is greater than the second thickness; the first thickness is measured from the inner surface of the bone anchor to the outer surface of the bone anchor and does not extend across the central aperture.

For example, see thicknesses 234, 235.

Example 14. The bone anchor system of claim 13 wherein the sidewall of the anchor system tapers away from the long axis of the bone anchor as the sidewall extends proximally towards the proximal tip and away from the distal tip.

For example, see taper angle 211.

Example 15. An bone anchor comprising: an outer housing; an inner housing, wherein at least a portion of the inner housing is located within the outer housing; wherein (a)(i) the outer housing includes a proximal third, a middle third, and a distal third, (a)(ii) the middle third of the outer housing includes at least one aperture that couples an outer surface of the outer housing to an inner surface of the outer housing; (a)(iii) an outer surface of the proximal third of the outer housing includes threads, and (a)(iv) an outer surface of the distal third of the outer housing includes threads; wherein (b)(i) the inner housing is cannulated, (b)(ii) the inner housing includes a channel, located on an outer surfaced of the inner housing, that extends from a proximal third of the inner housing to a distal third of the inner housing, and (b)(iii) the channel provides at least one half a rotation about a long axis of the inner housing.

For example, see FIG. 1C.

Example 16. The bone anchor of claim 15 wherein a plane, orthogonal to the long axis of the inner housing, intersects each of: (c)(i) at least one of the at least one aperture that couples the outer surface of the outer housing to the inner surface of the outer housing; and (c)(ii) the channel of the inner housing that extends from the proximal third of the inner housing to the distal third of the inner housing.

Example 17. The bone anchor of claim 16 comprising a distal aperture in the distal third of the outer housing, wherein the distal aperture is configured to advance bone particulate from outside the outer housing to the channel of the inner housing.

Another version of Example 17. The bone anchor of claim 16, wherein the bone anchor is a sacroiliac joint screw.

Example 17'. The bone anchor according to any of claims 15-16 comprising a distal aperture in the distal third of the outer housing, wherein the distal aperture is configured to advance bone particulate from outside the outer housing to the channel of the inner housing.

Example 18. An bone anchor comprising: an outer conduit; an inner conduit, wherein at least a portion of the inner conduit is located within the outer conduit; wherein (a)(i) the outer conduit includes a proximal third, a middle third, and a distal third, (a)(ii) the middle third of the outer conduit includes at least one aperture that couples an outer surface of the outer conduit to an inner surface of the outer conduit; (a)(iii) an outer surface of the proximal third of the outer conduit includes threads, and (a)(iv) an outer surface of the distal third of the outer conduit includes threads; wherein (b)(i) the inner conduit is cannulated, (b)(ii) the inner conduit includes a channel, located on an outer surfaced of the inner conduit, that extends from a proximal third of the inner conduit to a distal third of the inner conduit, and (b)(iii) the channel provides at least one half a rotation about a long axis of the inner conduit.

Example 19. The bone anchor of claim 18 wherein a plane, orthogonal to the long axis of the inner conduit, intersects each of: (c)(i) the outer conduit, (c)(ii) at least one of the at least one aperture that couples the outer surface of the outer conduit to the inner surface of the outer conduit; (c)(iii) the inner conduit, (c)(iv) the channel of the inner conduit that extends from the proximal third of the inner conduit to the distal third of the inner conduit.

Example 20. The bone anchor of claim 18 comprising a distal aperture in the distal third of the outer conduit, wherein the distal aperture is configured to advance bone particulate from outside the outer conduit to the channel of the inner conduit.

Another version of Example 20. The bone anchor of claim 18, wherein the bone anchor is a sacroiliac joint screw.

Example 20'. The bone anchor according to any of claims 18-19 comprising a distal aperture in the distal third of the outer conduit, wherein the distal aperture is configured to advance bone particulate from outside the outer conduit to the channel of the inner conduit.

Example 1a. A bone anchor system comprising: a bone anchor including an outer surface and an inner surface; wherein (a)(i) the outer surface includes a proximal third, a middle third, and a distal third, (a)(ii) the middle third of the outer surface includes at least one aperture that couples the outer surface to the inner surface; (a)(iii) the proximal third of the outer surface includes proximal threads, and (a)(iv) the distal third of the outer surface includes distal threads; wherein (b)(i) the bone anchor is cannulated, (b)(ii) a channel is located on the inner surface, (b)(iii) the channel extends from a proximal third of the inner surface to a distal third of the inner surface, and (b)(iii) the channel provides at least one half a rotation about a long axis of the bone anchor.

Example 2a. The bone anchor system of claim 1a wherein a plane, orthogonal to the long axis of the bone anchor, intersects each of: (c)(i) the outer surface, (c)(ii) at least one of the at least one aperture that couples the outer surface to the inner surface; and (c)(iii) the channel.

Example 3a. The bone anchor system according to any of claims 1a-2a comprising a distal aperture in a distal third of the bone anchor, wherein the distal aperture is configured to advance bone particulate from outside the bone anchor to the channel.

Example 4a. The bone anchor system according to any of claims 1a-3a, wherein the bone anchor is a compression screw.

Example 5a. The bone anchor system according to any of claims 1a-4a, wherein: the at least one aperture includes a first aperture and a second aperture; the first aperture includes a long axis parallel to the long axis of the bone anchor; the first aperture includes a short axis orthogonal to the long axis of the first aperture; the first aperture includes a length measured along the long axis and a width measured along the short axis; the length of the first aperture is greater than the width of the first aperture.

Example 6a. The bone anchor system of claim 5 wherein: an additional axis is parallel to the long axis of the bone anchor; the additional axis intersects the first and second apertures.

Example 7a. The bone anchor system according to any of claims 1a-6a comprising an additional channel located on the inner surface, wherein: (b)(i) the additional channel extends from the proximal third of the inner surface to the distal third of the inner surface, and (b)(ii) the additional channel provides at least one half a rotation about the long axis of the bone anchor.

Example 8a. The bone anchor system of claim 7 comprising a ridge on the inner surface, wherein: the ridge forms a wall of the channel; the ridge forms an additional wall of the additional channel.

Example 9a. The bone anchor system according to any of claims 1a-8a, wherein: the bone anchor includes a proximal tip and a distal tip; the distal third of the outer surface includes a distal aperture in addition to the at least one aperture; the distal aperture is between the proximal and distal tips of the bone anchor; the distal aperture directly connects to the channel; an opening of the distal aperture extends at least 1 mm proximally away from the distal tip and towards the proximal tip; the distal aperture is at least partially included in a sidewall of the bone anchor.

Example 10a. The bone anchor system of claim 9, wherein: the distal third of the outer surface includes an additional distal aperture in addition to the at least one aperture; the additional distal aperture is between the proximal and distal tips of the bone anchor; the additional distal aperture directly connects to the additional channel; the additional distal aperture is at least partially included in the sidewall of the bone anchor.

Example 11a. The bone anchor system according to any of claims 1a-10a wherein: the proximal threads include a first thread pitch which comprises a distance between crests of two adjacent threads; the distal threads include a second thread pitch; the first thread pitch is less than the second thread pitch.

Example 12a. The bone anchor system according to any of claims 1a-11a comprising a rod, wherein: the rod includes a long axis; the rod includes a short axis orthogonal to the long axis of the rod; the rod includes a length measured along the long axis of the rod and a width measured along the short axis of the rod; the bone anchor includes a central aperture defined by the inner surface of the bone anchor and the central aperture extends from the proximal tip of the bone anchor to the distal tip of the bone anchor; the central aperture includes a width measured along a short axis of the bone anchor, the short axis of the bone anchor being orthogonal to the long axis of the bone anchor; the width of the rod is less than the width of the central aperture; the width of the rod is at least 75% of the width of the central aperture.

Example 13a. The bone anchor system according to any of claims 9a-12a wherein: the sidewall of the bone anchor includes a first thickness included in a proximal third of the bone anchor; the sidewall of the bone anchor includes a second thickness included in a distal third of the bone anchor; the first thickness and the second thickness are both measured orthogonal to the long axis of the bone anchor; the first thickness is greater than the second thickness; the first thickness is measured from the inner surface of the bone anchor to the outer surface of the bone anchor and does not extend across the central aperture.

Example 14a. The bone anchor system according to any of claims 9a-13a wherein the sidewall of the anchor system tapers away from the long axis of the bone anchor as the sidewall extends proximally towards the proximal tip and away from the distal tip.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a certain side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first article "on" a second article is directly on and in immediate contact with the second article unless such is specifically stated; there may be a third article or other structure between the first article and the second article on the first article. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A bone anchor system comprising:

a bone anchor including an outer surface and an inner surface;

wherein (a)(i) the outer surface includes a proximal third, a middle third, and a distal third, (a)(ii) the middle third of the outer surface includes at least one aperture that couples the outer surface to the inner surface; (a)(iii) the proximal third of the outer surface includes proximal threads, and (a)(iv) the distal third of the outer surface includes distal threads;

wherein (b)(i) the bone anchor is cannulated, (b)(ii) first and second channels are located on the inner surface, (b)(iii) the first channel is included in a distal third of the inner surface and the second channel is included in a proximal third of the inner surface, and (b)(iv) each of the first and second channels rotates at least partially about a long axis of the bone anchor;

wherein the bone anchor includes a proximal tip and a distal tip;

wherein the distal third of the outer surface includes a distal aperture;

wherein the distal aperture is between the proximal and distal tips of the bone anchor;

wherein the distal aperture directly connects to the first channel;

wherein an opening of the distal aperture extends at least 1 mm proximally away from the distal tip and towards the proximal tip;

wherein the distal aperture is at least partially included in a sidewall of the bone anchor.

2. The bone anchor system of claim 1 wherein a plane, orthogonal to the long axis of the bone anchor, intersects each of: (c)(i) the outer surface, and (c)(ii) at least one of the at least one aperture that couples the outer surface to the inner surface.

3. The bone anchor system of claim 2, wherein:

the at least one aperture includes a first aperture and a second aperture;

the first aperture includes a long axis parallel to the long axis of the bone anchor;

the first aperture includes a short axis orthogonal to the long axis of the first aperture;

the first aperture includes a length measured along the long axis of the first aperture and a width measured along the short axis of the first aperture;

the length of the first aperture is greater than the width of the first aperture.

4. The bone anchor system of claim 3 wherein the plane intersects the first and second apertures.

5. The bone anchor system of claim 3 wherein: (b)(i) each of the first and second channels extends from the proximal third of the inner surface to the distal third of the inner surface, and (b)(ii) each of the first and second channels provides at least one half a rotation about the long axis of the bone anchor.

6. The bone anchor system of claim 1, wherein the bone anchor is a compression screw.

7. The bone anchor system of claim 1 comprising a ridge on the inner surface, wherein:

the ridge forms a wall of the first channel.

8. The bone anchor system of claim 1, wherein:

the distal third of the outer surface includes an additional distal aperture;

the additional distal aperture is between the proximal and distal tips of the bone anchor;

the additional distal aperture directly connects to a third channel;

the additional distal aperture is at least partially included in the sidewall of the bone anchor.

9. The bone anchor system of claim 8 wherein:

the proximal threads include a first thread pitch which comprises a distance between crests of two adjacent threads;

the distal threads include a second thread pitch;

the first thread pitch is less than the second thread pitch.

10. The bone anchor system of claim 9 comprising a rod, wherein:

the rod includes a long axis;

the rod includes a short axis orthogonal to the long axis of the rod;

the rod includes a length measured along the long axis of the rod and a width measured along the short axis of the rod;

the bone anchor includes a central aperture defined by the inner surface of the bone anchor;

the central aperture extends from the proximal tip of the bone anchor to the distal tip of the bone anchor;

the central aperture includes a width measured along a short axis of the bone anchor, the short axis of the bone anchor being orthogonal to the long axis of the bone anchor;

the width of the rod is less than the width of the central aperture;

the width of the rod is at least 75% of the width of the central aperture.

11. The bone anchor system of claim 9 wherein:

the sidewall of the bone anchor includes a first thickness included in a proximal third of the bone anchor;

the sidewall of the bone anchor includes a second thickness included in a distal third of the bone anchor;

the first thickness and the second thickness are both measured orthogonal to the long axis of the bone anchor;

the first thickness is greater than the second thickness;

the first thickness is measured from the inner surface of the bone anchor to the outer surface of the bone anchor and does not extend across the at least one aperture.

12. The bone anchor system of claim 11 wherein the sidewall of the bone anchor system tapers away from the long axis of the bone anchor as the sidewall extends proximally towards the proximal tip and away from the distal tip.

13. A bone anchor system comprising:

a cannulated bone anchor including outer and inner surfaces and proximal and distal tips;

wherein (a)(i) the outer surface includes proximal, middle, and distal thirds, (a)(ii) the middle third of the outer surface includes at least one aperture that couples the outer surface to the inner surface; (a)(iii) the proximal third of the outer surface includes proximal threads and the distal third of the outer surface includes distal threads;

wherein (b)(i) a first channel is included in a distal third of the inner surface and a second channel is included in a proximal third of the inner surface, and (b)(ii) each of the first and second channels rotates about a long axis of the bone anchor;

wherein the distal third of the outer surface includes a distal aperture: (c)(i) between the proximal and distal tips of the bone anchor, (c)(ii) directly connected to the first channel, (c)(iii) having an opening extending at least 1 mm proximally away from the distal tip, and (c)(iv) at least partially included in a sidewall of the bone anchor.

14. The bone anchor system of claim 13, wherein:

the distal third of the outer surface includes an additional distal aperture;

the additional distal aperture is between the proximal and distal tips of the bone anchor;

the additional distal aperture directly connects to a third channel included in the distal third of the inner surface;

the additional distal aperture is at least partially included in the sidewall of the bone anchor.

15. The bone anchor system of claim 14 wherein:

the proximal threads include a first thread pitch which comprises a distance between crests of two adjacent threads;

the distal threads include a second thread pitch;

the first thread pitch is less than the second thread pitch.

16. The bone anchor system of claim 15 comprising a rod, wherein:

the rod includes a long axis;

the rod includes a short axis orthogonal to the long axis of the rod;

the rod includes a length measured along the long axis of the rod and a width measured along the short axis of the rod;

the bone anchor includes a central aperture defined by the inner surface of the bone anchor;

the central aperture extends from the proximal tip of the bone anchor to the distal tip of the bone anchor;

the central aperture includes a width measured along a short axis of the bone anchor, the short axis of the bone anchor being orthogonal to the long axis of the bone anchor;

the width of the rod is less than the width of the central aperture;

the width of the rod is at least 75% of the width of the central aperture.

17. The bone anchor system of claim 15 wherein:

the sidewall of the bone anchor includes a first thickness included in a proximal third of the bone anchor;

the sidewall of the bone anchor includes a second thickness included in a distal third of the bone anchor;

the first thickness and the second thickness are both measured orthogonal to the long axis of the bone anchor;

the first thickness is greater than the second thickness;

the first thickness is measured from the inner surface of the bone anchor to the outer surface of the bone anchor and does not extend across the at least one aperture.

18. The bone anchor system of claim 17 wherein the sidewall of the bone anchor system tapers away from the long axis of the bone anchor as the sidewall extends proximally towards the proximal tip and away from the distal tip.

19. The bone anchor system of claim 18, wherein the bone anchor is a compression screw.

* * * * *